United States Patent [19]
Shen et al.

[11] Patent Number: 6,143,919
[45] Date of Patent: Nov. 7, 2000

[54] POLYMERIZABLE ACIDIC COMPOUNDS AND METHODS OF PREPARATION

[75] Inventors: Byron Ciping Shen, Woodbury; Charles M. Leir, Falcon Heights; Amy M. DeVries, New Brighton, all of Minn.

[73] Assignee: 3M Innovative Properties Company, St. Paul, Minn.

[21] Appl. No.: 09/314,489

[22] Filed: May 18, 1999

[51] Int. Cl.⁷ .................................................. C07C 271/22
[52] U.S. Cl. ........................................ 560/158; 560/160
[58] Field of Search ..................................... 560/158, 160

[56] References Cited

U.S. PATENT DOCUMENTS

| | | |
|---|---|---|
| 3,655,605 | 4/1972 | Smith . |
| 3,814,717 | 6/1974 | Wilson et al. . |
| 4,143,018 | 3/1979 | Crisp et al. . |
| 4,144,324 | 3/1979 | Crutchfield et al. . |
| 4,208,401 | 6/1980 | Bauman . |
| 4,209,434 | 6/1980 | Wilson et al. . |
| 4,360,605 | 11/1982 | Schmitt et al. . |
| 4,376,835 | 3/1983 | Schmitt et al. . |
| 4,383,052 | 5/1983 | Higo et al. . |
| 4,394,494 | 7/1983 | Miyake et al. . |
| 4,407,761 | 10/1983 | Blum et al. . |
| 4,503,169 | 3/1985 | Randklev . |
| 4,639,338 | 1/1987 | Stahl et al. . |
| 4,695,251 | 9/1987 | Randklev . |
| 4,732,998 | 3/1988 | Binderup . |
| 4,877,401 | 10/1989 | Higuchi et al. . |
| 4,877,603 | 10/1989 | Degenhardt et al. . |
| 5,015,180 | 5/1991 | Randklev . |
| 5,019,651 | 5/1991 | Kieczykowski . |
| 5,096,699 | 3/1992 | Gaffar et al. . |
| 5,130,347 | 7/1992 | Mitra . |
| 5,162,310 | 11/1992 | Jaeggi . |
| 5,204,426 | 4/1993 | Ellis et al. . |
| 5,208,009 | 5/1993 | Gaffar et al. . |
| 5,218,070 | 6/1993 | Blackwell . |
| 5,258,067 | 11/1993 | Podszun et al. . |
| 5,260,483 | 11/1993 | Davis et al. . |
| 5,270,365 | 12/1993 | Gertz et al. . |
| 5,332,429 | 7/1994 | Mitra et al. . |
| 5,354,199 | 10/1994 | Jacobs et al. . |
| 5,441,945 | 8/1995 | Yoshikawa . |
| 5,451,401 | 9/1995 | Zerby et al. . |
| 5,525,648 | 6/1996 | Aasen et al. . |
| 5,547,379 | 8/1996 | Hasel . |
| 5,652,227 | 7/1997 | Teronen et al. . |
| 5,665,120 | 9/1997 | Ohtsuka et al. . |

FOREIGN PATENT DOCUMENTS

| | | |
|---|---|---|
| WO 97/18791 | 5/1997 | WIPO . |
| WO 97/18792 | 5/1997 | WIPO . |
| WO 98/43596 | 10/1998 | WIPO . |
| WO 98/46197 | 10/1998 | WIPO . |
| WO 99/03444 | 1/1999 | WIPO . |

OTHER PUBLICATIONS

Y. Imai et al., "Preparation and Properties of Hydrophilic Methacrylate Monomers," *New Functionality Materials, Vol. B, Synthesis and Function Control of Biofunctionality Materials*, 1993, p. 43.

Simmelink, J.W., "Ultrastructural Effects of Diphosphonates on Dental Enamel," *Adv. Dent. Res.*, vol. 1 No. 2, Dec. 1987, p. 356.

Anbar, M. et al., "Potential Use of Organic Polyphosphonates as Adhesives in the Restoration of Teeth," *J. Dent. Res.*, vol. 53 No. 4, Jul.–Aug. 1974, p. 879.

Anbar, M. et al., "Improved Adhesion of Acrylic Restorative Materials to Dental Enamel by Precoating with Monomers Containing Phosphonate Groups," *J. Dent. Res.*, vol. 56, No. 8, Aug. 1977, p. 943.

Anbar, M. et al., "Organic Polymeric Polyphosphonates as Potential Preventive Agents of Dental Caries: In Vitro Experiments," *J. Dent. Res.*, vol. 53, No. 4, 5, Jul.–Aug., Sep.–Oct., 1974, p. 867, 1240.

Anbar, M. et al., "Adsorption of Polyphosphonated Polyethylene on Enamel of Teeth," *J. Dent. Res.*, vol. 50, No. 3, May–Jun. 1971, p. 778.

Saunders, J.H. and Frisch, K.C., Polyurethanes Chemistry and Technology, Part I., Chemistry, 1962, pp. 73–75, 80–81.

Anbar, M. et al., "Adsorption of Polyphosphonated Polyethylene on Enamel of Teeth," *J. Dent. Res.*, vol. 50, No. 3, May–Jun. 1971, p. 778.

*Primary Examiner*—Gary Geist
*Assistant Examiner*—Leigh C. Maier

[57] ABSTRACT

Polymerizable urethane acid compounds are provided. Preferred compounds additionally comprise a hydroxy functionality. These compounds are made by reaction of hydroxy functional acid compounds with isocyanates.

18 Claims, No Drawings

POLYMERIZABLE ACIDIC COMPOUNDS AND METHODS OF PREPARATION

FIELD OF THE INVENTION

The present invention relates to new polymerizable urethane acids. More specifically, the present invention relates to multi-functional compounds that may be generated by a highly selective reaction.

BACKGROUND

Polymerizable acidic materials have previously been used in resin bonding systems and in hybrid cement systems. For example, polymerizable acidic materials are described in U.S. Pat. No. 5,130,347 for use in glass ionomer cements. Such compounds are also described for use in dental adhesives in U.S. Pat. No. 5,525,648.

SUMMARY OF THE INVENTION

Novel polymerizable urethane acid compounds of the present invention have the formula:

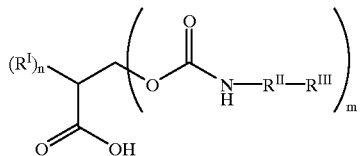

wherein n is 0, 1 or 2 m is 1, 2 or 3 and n+m=3;

$R^I$ is independently, $C_{1-22}$ alkyl, —O—$C_{1-12}$ alkyl; $C_{1-12}$ alkyl—OH;

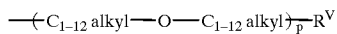

$R^V$=alkyl or —OH with the proviso that when m=1, one of $R^I$ is —CH$_2$OH $R^{II}$ is independently

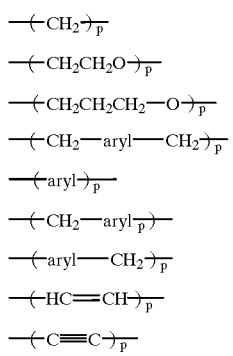

wherein p is 1–12 or any combination thereof $R^{III}$ is independently

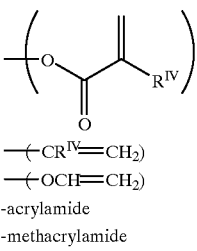

—(—$CR^{IV}$=CH$_2$)
—(—OCH=CH$_2$)
-acrylamide
-methacrylamide $R^{IV}$ is independently H, C1–12 alkyl.

Novel preparations of these compounds are also described.

DETAILED DESCRIPTION OF THE INVENTION

The polymerizable urethane acids of the present invention have several advantages in comparison with previously known acidic monomers. Materials, especially dental materials, comprising these polymerizable acidic monomers exhibit high strength and toughness of the cured (crosslinked) material. Further, the present polymerizable acidic monomer is relatively low in viscosity as compared to previously prepared polymerizable acidic monomers. The present invention therefore allows formulation of materials, such as dental materials, having a higher percentage of polymerizable acidic monomer in the material than previously possible at a desired viscosity or consistency. Unlike monomers recommended for use in the prior art for cement systems that contain multiple acid groups, the present polymerizable urethane acids have only one carboxylic acid group. It has been found that in the glass-ionomer or compomer type formulations, having only one acid group helps to improve the stability of the paste. Further, unlike many other polyfunctional monomers which are often a mixture of different components, the present polymerizable acid monomers can be produced in high purity. High purity is extremely helpful in achieving a consistent manufacturing process and making consistent end products.

The polymerizable acid monomers of this invention are useful components in various dental materials where acid functionality is desired, such as compomers, composites, flowable composites, glass ionomers, resin cements, and dental adhesives. These monomers also have applications in other industrial or biomedical adhesive products.

Certain molecules of the present invention provide polymerizable chelating monomers. The β-hydroxyl carboxylic acid moiety on this molecule is capable of chelating metal ions, e.g., Calcium, so that a six-membered ring will form. The β-hydroxyl carboxylic acid compounds of the present invention thus provide surprisingly good surface treatment activity as compared to materials that do not contain the β-hydroxyl carboxylic acid combination of functionalities, while being polymerizable to provide a material that does not contain free acid monomers after polymerization of the overall resin. This material is therefore highly desirable for use in adhesive compositions, and substantially reduces or eliminates the need for prior surface treatment before bonding to the surface. The β-hydroxyl carboxylic acid compounds of the invention are also highly reactive with acid reactive glass, facilitating rapid cement reactions.

The polymerizable acid monomers of this invention are also useful as intermediates for other useful materials. For example, acidic polymerizable monomers of the present invention may be reacted with a metal fluoride, such as ZnF2, SnF2, A1F3, thereby preparing useful metal fluoro-complexes. These metal fluoro-complexes could then be used as additives in dental materials for fluoride release.

Alternatively, polymerizable acid monomers of this invention have at least one (and in the case of hydroxy functional compounds, two) active hydrogen site capable of further reaction to provide polymerizable materials having unique chemical structure for incorporation in polymerizable resins.

For example, the further functionalization of the hydroxyl groups on the hydroxy functional polymizable acidic monomers of the present invention may be carried out in alternative conversion routes. For example, the hydroxyl groups may be converted into methacrylate groups directly via reaction with methacrylic acid or methacryl chloride; or in reacting with the epoxy groups in glycidyl methacrylate. Similarly, the present monomers may also be useful for making compounds having various spacers (e.g., aromatic groups, ethylene oxide units, more than two urethane linkages) in-between various functional groups and the propionic acid moiety.

Of the compounds described above, one preferred class of compounds has the formula:

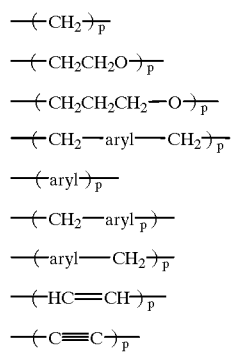

wherein
n is 2
m is 1
one of $R^I$ is —$CH_2OH$;
and the other of $R^I$ is $C_{1-12}$ alkyl, —O—$C_{1-12}$ alkyl;

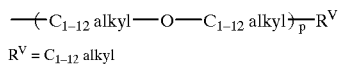

$R^{II}$ is independently

—$(CH_2)_p$—
—$(CH_2CH_2O)_p$—
—$(CH_2CH_2CH_2—O)_p$—
—$(CH_2—aryl—CH_2)_p$—
—$(aryl)_p$—
—$(CH_2—aryl)_p$—
—$(aryl—CH_2)_p$—
—$(HC=CH)_p$—
—$(C\equiv C)_p$— wherein p is 1–12
or any combination thereof $R^{III}$ is independently

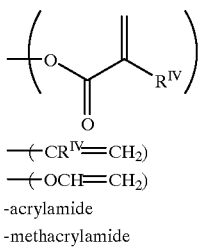

—$(CR^{IV}=CH_2)$
—$(OCH=CH_2)$
-acrylamide
-methacrylamide $R^{IV}$ is independently H, C1–12 alkyl.

Another preferred class of compounds has the formula:

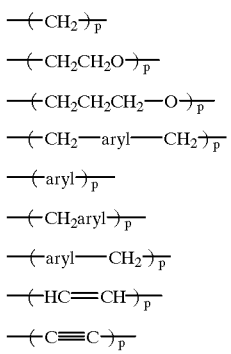

wherein
n is 1
m is 2
$R^I$ is $C_{1-12}$ alkyl, —O—$C_{1-12}$ alkyl;

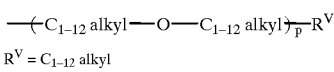

$R^{II}$ is independently

—$(CH_2)_p$—
—$(CH_2CH_2O)_p$—
—$(CH_2CH_2CH_2—O)_p$—
—$(CH_2—aryl—CH_2)_p$—
—$(aryl)_p$—
—$(CH_2aryl)_p$—
—$(aryl—CH_2)_p$—
—$(HC=CH)_p$—
—$(C\equiv C)_p$— wherein p is 1–12
or any combination thereof
$R^{III}$ is independently

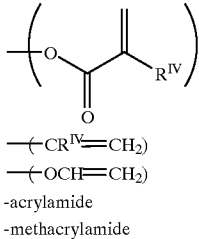

—$(CR^{IV}=CH_2)$
—$(OCH=CH_2)$
-acrylamide
-methacrylamide $R^{IV}$ is independently H, C1–12 alkyl.

A particularly preferred class of compounds of the present invention is
wherein n = 1;
m = 2;
$R^I$ = $CH_3$;
$R^{II}$ = —(CH₂CH₂)—;

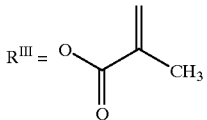

Another particularly preferred class are the compounds wherein n=2, m=1, one of $R^I$ is $CH_2$—OH and the other $R^I$ is —$CH_3$, $R^{II}$ is

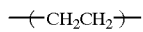

and $R^{III}$ is

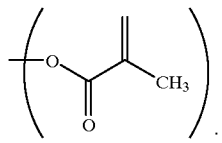

Another particularly preferred class of compounds is where n is 2 and one of $R^I$ is $CH_2$—OH.

Most preferably, the polymerizable carboxylic acid compound is selected from 2,2-di(N-methacryloxyethyl carbamoylmethyl)propionic acid ("PDMA") and 2-hydroxymethyl-2-[(N-methacryloxyethyl) carbamoylmethyl] propionic acid ("PAMA").

Another aspect of the present invention provides a method of making compounds of the formula:

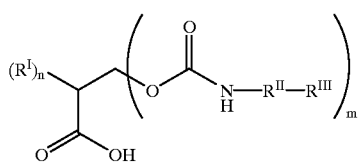

wherein
n is 2
m is 1
one of $R^I$ is —$CH_2OH$;
and the other of $R^I$ is $C_{1-12}$ alkyl, —O—$C_{1-12}$ alkyl;

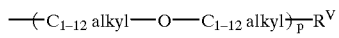

$R^{II}$ is independently

—(CH₂)ₚ—
—(CH₂CH₂O)ₚ—
—(CH₂CH₂CH₂—O)ₚ—

-continued
—(CH₂—aryl—CH₂)ₚ—
—(aryl)ₚ—
—(CH₂—aryl)ₚ—
—(aryl—CH₂)ₚ—
—(HC=CH)ₚ—
—(C≡C)ₚ— wherein p is 1–12
or any combination thereof
$R^{III}$ is independently

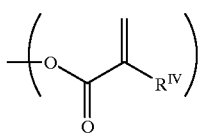

—(CR^{IV}=CH₂)
—(OCH=CH₂)
-acrylamide
-methacrylamide $R^{IV}$ is independently H, C1–12 alkyl.
In this method, a compound of the formula

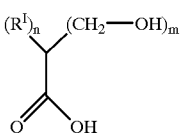

wherein the substituents are as defined immediately above, is reacted with a compound of the formula

O=C=N—(R^{II})—R^{III} wherein the substituents are as defined immediately above.

These compounds are reacted in the presence of a catalytic amount of a non-basic catalyst at a temperature between about 40 and 80° C. for a time greater than about 15 hours.

Surprisingly, it has been found that undertaking this reaction as described above generates a high yield of the desired mono-hydroxy functional polymerizable acid. This is unexpected in view of the otherwise rapid reaction of isocyanato with primary hydroxyl compounds, such as disclosed in Saunders and Frisch, Polyurethanes Chemistry and Technology, (1962 John Wiley and Sons), pp. 73–75, 80–81. One would have expected all of the hydroxyl compounds to react under the present aggressive conditions. This yield is far higher than the statistically expected yield, with in excess of 80% of the reaction product being the desired material, with less than 20% of the reaction product being the bis-polymerizable compound (generated by reaction of the isocyanate with both hydroxyl functionalities) and amido functional product (generated by reaction of the isocyanate with the acid functionality). More preferably, the reaction generates an excess of 85% of the reaction product being the desired desired mono-hydroxy functional polymerizable acid. This result is in surprising contrast to the expected reaction product distribution, which would be expected to be a statistical distribution of reaction of the isocyanate with alcohols, resulting in about 66% of the mono-hydroxy functional compound and 33% of the bis-polymerizable compound. One would further expect that any amido-functional compound would act only to reduce the yield of the desired product proportionally.

Because no base is used as a catalyst, the present reaction provides the significant benefit of not forming the salt of the acid, which would have to be reconverted back to the acid before use in the ultimate system where an acid is desired.

Preferred non-basic catalysts for use in the present invention include tin IV catalysts, such as dibutyltin dilaurate, dibutyltin diacetate, dibutyltin dilaurate, dibutyltin dimercaptide, dibutyltin dithioglycolate, dimethyltin dilaurate, dimethyltin dimaleate, dimethyltin dimercaptide, dimethyltin dithioglycolate, dioctyltin dilaurate, dioctyltin dimercaptide, and dioctyltin dithioglycolate. Other tin II catalysts include stannous octoate and stannous stearate. Other urethane metal catalysts include bismuth neodecanoate, phenylmercuric propionate, potassium octoate, and zinc stearate.

Preferably, this reaction is carried out such that the molar ratio of the hydroxy acid starting material to the isocyanate starting material is greater than about 1:1. This reaction condition provides a final product that is a mixture of mono and di polymerizable functional compounds, with a predominant amount of the mono-polymerizable functional compound.

In another preferred reaction, the reaction is carried out such that the molar ratio of the hydroxy acid starting material to the isocyanate starting material is greater than about 2:1. This reaction condition provides a final product that is a mixture of mono- and di- polymerizable functional compounds, with a surprisingly high predominance of the mono-polymerizable functional compound.

A further surprising aspect of the present invention is the method of making compounds of the formula:

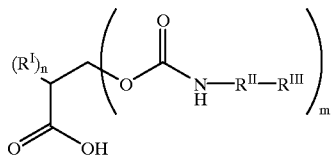

wherein
n is 1
m is 2
$R^I$ is $C_{1-12}$ alkyl, —O—$C_{1-12}$ alkyl;

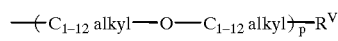

$R^{II}$ is independently

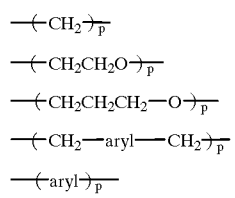

—(—aryl—$CH_2$—)$_p$—

—(—HC=CH—)$_p$—

—(—C≡C—)$_p$— wherein p is 1–12
or any combination thereof
$R^{III}$ is independently

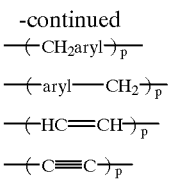

—(—$CR^{IV}$=$CH_2$)

—(—OCH=$CH_2$)

-acrylamide

-methacrylamide $R^{IV}$ is independently H, C1–12 alkyl.

This compound is provided by reacting one part of a compound of the formula

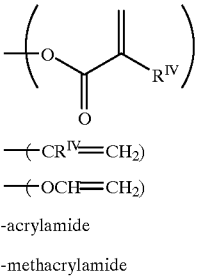

wherein the substituents are as defined immediately above, with two parts of a compound of the formula

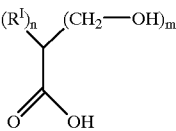

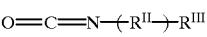

wherein the substituents are as defined immediately above.

These reactants are reacted in the presence of a hydroxyl/isocyanato reaction catalyst at a temperature between about 22 and 80° C. for a time greater than about 15 hours when only non-basic catalyst is used. The hydroxyl/isocyanato reaction catalyst for this reaction may be an organic basic catalyst, a non-basic catalyst or combinations thereof. Preferably, the catalyst is a non-basic catalyst.

Under these reaction conditions, one would expect that the acid functionality would be either destroyed through the harsh reaction conditions, or the isocyanate would react with the acid to form an amide or a urea. Such amide or urea formation reactions have previously been observed using different starting materials to be a reasonably rapid reaction under less aggressive conditions. An example of such a reaction at room temperature is disclosed in U.S. Pat. No. 5,260,483.

Preferred organic basic catalysts are the tertiary amine catalysts, including triethylamine; triethylenediamine; bis(dimethylaminoethyl) ether; tris(dimethylaminomethyl) phenol; N,N'-dimorpholinodiethyl ether; N,N'-dimethyl cyclohexylamine; pentamethyl N,N'-dipropylenetriamine; 1,8-diazabicyclo-[5,4,0]-undecane 7, N,N'-dimethylethanol amine; and N-ethylmorpholine.

The following examples are provided for purposes of illustrating the present invention, and are not intended to be limiting of the broadest concepts of the present invention. Unless otherwise indicated, all parts and percentages are by weight and all molecular weights are weight average molecular weight.

EXAMPLES

Example 1

2,2-di(N-methacryloxyethyl carbamoylmethyl) propionic acid (PDMA) is synthesized by reacting 2,2-Bis (hydroxymethyl)propionic acid (BHMPA) and two equivalents of Isocyanatoethylmethacrylate (IEM) as follows:

2,2-Bis(hydroxymethyl)propionic acid (BHMPA, 225.21 g, 1.679 mole), small amounts of stabilizer(s) such as 2,6-Di-tert-butyl-4-methylphenol (BHT, 1.6781 g, 7.615 mmole) and/or Triphenyl antimony (TPS, 1.3463 g, 3.813 mmole), and a catalytic amount of Dibutlytin dilaurate (2.4396 g, 3.863 mmole) and dry THF or other suitable solvents were added first to the reactor. After the solution was stirred for a short while, IEM (592.64 g, 3.823 mole) was added. The reaction was heated to 65° C. for about 30 hours while stirring constantly. The solvent was stripped off after the conversion was completed. The final product, PDMA, was a colorless, viscous liquid.

Example 2

Alternatively, the above reaction can be carried out using Triethylamine as a base catalyst to speed up the reaction. 0.075 to 0.15 Equivalent of Triethylamine is typically needed. This reaction was undertaken as follows:

2,2-Bis(hydroxymethyl)propionic acid (14.9946 g, 0.112 mole), small amounts of 2,6-Di-tert-butyl-4-methylphenol (0.1012 g, 0.456 mmole) stabilizer [an alternative stablizer, such as Triphenyl antimony (0.0831 g, 0.235 mmole) may be used], and a catalytic amount of Dibutlytin dilaurate (0.1450 g, 0.230 mmole), Triethylamine (1.132 g, 0.0112 mole) and dry THF were added first to the reactor. After the solution was stirred for a short while, IEM (35.55 g, 0.229 mole) was added. The reaction was heated to 65° C. for 8 hours while stirring constantly. After the functionalization step, the triethylamine was removed by re-acidifying with 37% wt aq. HCl (1.218 g, 0.0124 mole) at low temperature. A white solid, triethylamine hydrochloride, precipitated out. After filtering out the white precipitate while the solution was still cold, the solvent was then stripped off. Re-acidification is not necessary if the presence of a small amount of triethylamine can be tolerated in a given application.

Example 3

The reactor was first charged with an excess amount of BHMPA (139.94 g, 1.043 mole), 2,6-Di-tert-butyl-4-methylphenol (0.2322 g, 1.054 mmole), Triphenyl antimony (0.1891 g, 0.536 mmole), and Dibutlytin dilaurate (0.6801 g, 1.077 mmole). The starting material, BHMPA, was only slightly soluble in THF at room temperature. IEM was gradually dripped (80.94 g, 0.522 mole) into the above mixture. The reaction was run at 60° C. for 24 hours while stirring constantly. At the end of the reaction, most of the unreacted BHMPA settled out as white solid powder after the solution was cooled down. Unreacted BHMPA was filtered off by vacuum filtration, and the solvent was then stripped off. The recovered BHMPA could be used in future reactions.

After the removal of the solvent, the product became slightly cloudy due to slow precipitation of residual BHMPA. Enough diethyl ether was added to dissolve the product and then the solution was allowed to sit overnight (approximately 18 hours) undisturbed to precipitate out most of the remaining BHMPA in solution. The white precipitate was filtered off by vacuum filtration, and diethyl ether was stripped off.

The resulting product, PAMA was a colorless, flowable liquid. The purity of PAMA in the final product was approximately 80% by molar ratio, with PDMA being the main side-product (approximately 17%) and small amounts of remaining BHMPA (approximately 3%).

What is claimed is:

1. A compound of the formula

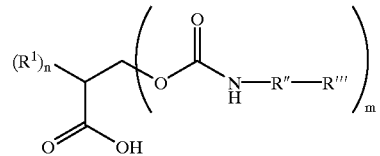

wherein n is 0, 1 or 2 m is 1, 2 or 3 and n+m=3;

$R^I$ is independently, $C_{1-12}$ alkyl, —O—$C_{1-12}$ alkyl; $C_{1-12}$ alkyl—OH;

—$(C_{1-12}$ alkyl—O—$C_{1-12}$ alkyl$)_p$—$R^V$ $R^V$=$C_{1-12}$ alkyl  or  —OH with the proviso that when m=1, one of $R^I$ is —$CH_2OH$ $R^{II}$ is independently —$(CH_2)_p$—    —$(CH_2CH_2O)_p$—

—$(CH_2CH_2CH_2—O)_p$—    —$(CH_2—aryl—CH_2)_p$—

—$(aryl)_p$—    —$(CH_2aryl)_p$—    —$(aryl—CH_2)_p$—

—$(HC=CH)_p$—    —$(C≡C)_p$— wherein p is 1–12 or any combination thereof $R^{III}$ is independently $-(O-\underset{O}{\underset{\|}{C}}-\underset{R^{IV}}{\overset{CH_2}{\|}})-$    —$(CR^{IV}=CH_2)$ —$(OCH=CH_2)$    —acrylamide    —methacrylamide $R^{IV}$ is independently H, C1–12 alkyl;
or a salt thereof.

2. The compound of claim 1, having the formula:

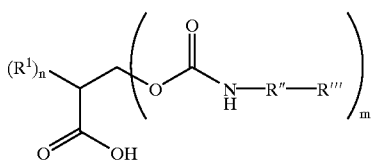

wherein
n is 2
m is 1
one of $R^I$ is —CH$_2$OH;
and the other of $R^I$ is C$_{1-12}$ alkyl, —O—C$_{1-12}$ alkyl;

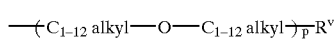

$R^{II}$ is independently

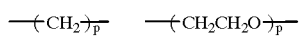

wherein p is 1–12
or any combination thereof
$R^{III}$ is independently

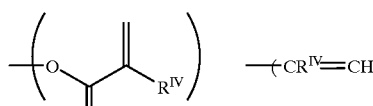 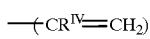

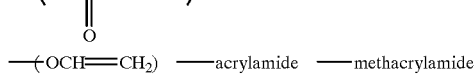

$R^{IV}$ is independently H, C$_{1-12}$ alkyl.

3. The compound of claim 1, having the formula;

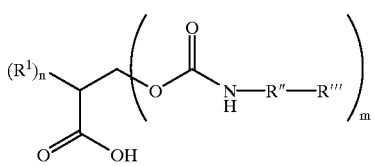

wherein
n is 1
m is 2
$R^I$ is C$_{1-12}$ alkyl, —O—C$_{1-12}$ alkyl;

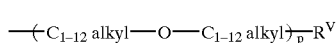
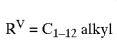

$R^{II}$ is independently

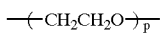
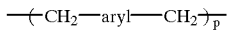
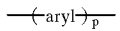
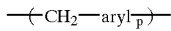
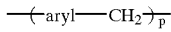

wherein p is 1–12
or any combination thereof
$R^{III}$ is independently

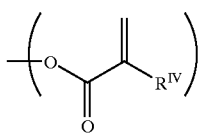

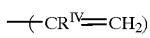

-acrylamide

-methacrylamide $R^{IV}$ is independently H, C1–12 alkyl.

4. The compound of claim 1 wherein
n=1;
m=2;
$R^I$=CH$_3$;

$R^{II}$ = —(CH$_2$CH$_2$)—;

$R^{III}$ = 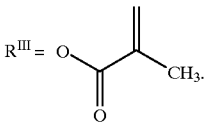

5. The compound of claim 1, wherein
n=2, m=1, one of $R^I$ is CH$_2$—OH
and the other $R^I$ is —CH$_3$, $R^{II}$ is —(CH$_2$CH$_2$)— and $R^{III}$ is

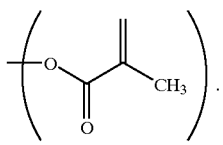.

6. The compound of claim 1, wherein n is 2 and one of $R^I$ is CH$_2$—OH.

7. The compound of claim 1, which is 2,2-di(N-methacryloxyethyl carbamoylmethyl) propionic acid (PDMA).

8. The compound of claim 1, which is 2-hydroxymethyl-2-[(N-methacryloxyethyl) carbamoylmethyl] propionic acid ("PAMA").

9. A method of making compounds of the formula:

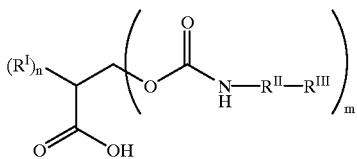

wherein
n is 2
m is 1
one of $R^I$ is —CH$_2$OH;
and the other of $R^I$ is C$_{1-12}$ alkyl, —O—C$_{1-12}$ alkyl;

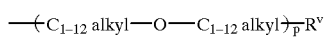

$R^{II}$ is independently

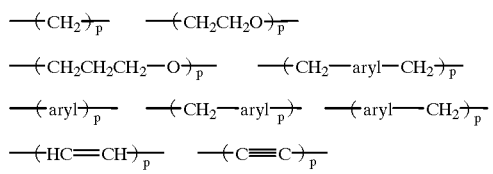

wherein p is 1–12
or any combination thereof
$R^{III}$ is independently

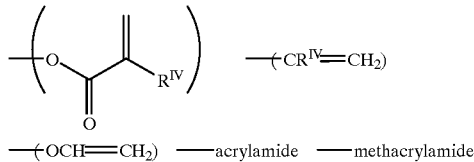

$R^{IV}$ is independently H, C1–12 alkyl said method comprising reacting a compound of the formula

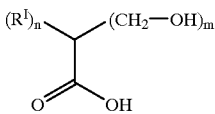

wherein the substituents are as defined immediately above, with a compound of the formula

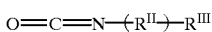

wherein the substituents are as defined immediately above, said reaction being in the presence of a catalytic amount of a non-basic catalyst at a temperature between about 22 and 80° C. for a time greater than about 15 hours, said reaction generating an excess of 80% of the theoretical yield of the mono-hydroxy functional polymerizable acid.

10. The method of claim 9, wherein the reaction generates an excess of 85% of the theoretical yield of the mono-hydroxy functional polymerizable acid.

11. The method of claim 9, wherein said non-basic catalyst is selected from the group consisting of tin IV catalysts and tin II catalysts.

12. The method of claim 9, wherein said non-basic catalyst is selected from the group consisting of dibutyltin dilaurate, dibutyltin diacetate, dibutyltin dilaurate, dibutyltin dimercaptide, dibutyltin dithioglycolate, dimethyltin dilaurate, dimethyltin dimaleate, dimethyltin dimercaptide, dimethyltin dithioglycolate, dioctyltin dilaurate, dioctyltin dimercaptide, and dioctyltin dithioglycolate, stannous octoate, stannous stearate, bismuth neodecanoate, phenylmercuric propionate, potassium octoate, and zinc stearate.

13. The method of claim 9, wherein the molar ratio of the compound of the hydroxy acid starting material to the isocyanate starting material is greater than about 1:1.

14. The method of claim 9, wherein the molar ratio of the compound of the hydroxy acid starting material to the isocyanate starting material is greater than about 2:1.

15. A method of making compounds of the formula:

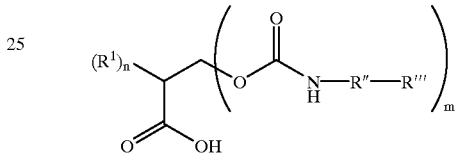

wherein
n is 1
m is 2
$R^I$ is C$_{1-12}$ alkyl, —O—C$_{1-12}$ alkyl;

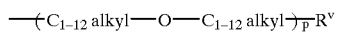

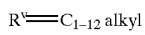

$R^{II}$ is independently

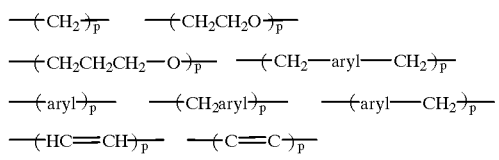

wherein p is 1–12
or any combination thereof
$R^{III}$ is independently

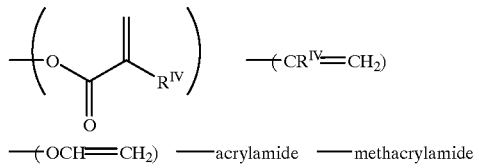

$R^{IV}$ is independently H, C1–12 alkyl, comprising reacting a compound of the formula

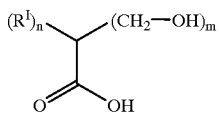

wherein the substituents are as defined immediately above, with a compound of the formula

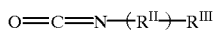

wherein the substituents are as defined immediately above, at a temperature between about 22 and 80° C. for a time greater than about 15 hours, wherein said reaction generates less than 5% amide and urea reaction products of the theoretical yield of products.

16. The method of claim 15, wherein said reaction takes place in the presence of a hydroxyl/isocyanate reaction catalyst.

17. The method of claim 16, wherein said hydroxyl/isocyanate reaction catalyst is an organic basic catalyst is selected from the group consisting of tertiary amine catalysts.

18. The method of claim 17, wherein the tertiary amine catalyst is selected from the group consisting of triethylamine; triethylenediamine; bis(dimethylaminoethyl) ether; tris(dimethylaminomethyl) phenol; N,N'-dimorpholinodiethyl ether; N,N'-dimethyl cyclohexylamine; pentamethyl dipropylenetriamine; 1,8-diazabicyclo-[5,4,0]-undecane 7, N,N'-dimethylethanol amine; and N-ethylmorpholine.

* * * * *

UNITED STATES PATENT AND TRADEMARK OFFICE
CERTIFICATE OF CORRECTION

PATENT NO.    : 6,143,919
DATED         : November 7, 2000
INVENTOR(S)   : Shen, Byron C.

It is certified that error appears in the above-identified patent and that said Letters Patent is hereby corrected as shown below:

Title page,
Item [56], OTHER PUBLICATIONS, delete "Anbar, M. et al., "Adsorption of Polyphosphonated Poly-ethylene on Enamel of Teeth," *J. Dent. Res.*, vol. 50, No. 3, May-Jun. 1971, p. 778.".

Column 1,
Line 40, delete "$C_{1-22}$" and insert in place thereof -- $C_{1-12}$ --.

Signed and Sealed this

Twenty-ninth Day of October, 2002

Attest:

Attesting Officer

JAMES E. ROGAN
*Director of the United States Patent and Trademark Office*